(12) United States Patent
Cho et al.

(10) Patent No.: US 10,765,669 B2
(45) Date of Patent: Sep. 8, 2020

(54) PHARMACEUTICAL COMPOSITION FOR PREVENTING OR TREATING DYRK-RELATED DISEASES, CONTAINING PYRIDINE-BASED COMPOUND AS ACTIVE INGREDIENT

(71) Applicants: KOREA RESEARCH INSTITUTE OF BIOSCIENCE AND BIOTECHNOLOGY, Daejeon (KR); KOREA RESEARCH INSTITUTE OF CHEMICAL TECHNOLOGY, Daejeon (KR)

(72) Inventors: Sungchan Cho, Daejeon (KR); Miri Choi, Daejeon (KR); Joo Youn Lee, Daejeon (KR)

(73) Assignees: KOREA RESEARCH INSTITUTE OF BIOSCIENCE AND BIOTECHNOLOGY, Daejeon (KR); KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 16/470,014

(22) PCT Filed: Dec. 15, 2017

(86) PCT No.: PCT/KR2017/014893
§ 371 (c)(1),
(2) Date: Jun. 14, 2019

(87) PCT Pub. No.: WO2018/111049
PCT Pub. Date: Jun. 21, 2018

(65) Prior Publication Data
US 2020/0085803 A1 Mar. 19, 2020

(30) Foreign Application Priority Data

Dec. 15, 2016 (KR) .................. 10-2016-0171495
Dec. 14, 2017 (KR) .................. 10-2017-0172214

(51) Int. Cl.
*A61K 31/381* (2006.01)
*A61K 31/444* (2006.01)
*A23L 33/10* (2016.01)

(52) U.S. Cl.
CPC ............ *A61K 31/444* (2013.01); *A23L 33/10* (2016.08); *A23V 2002/00* (2013.01)

(58) Field of Classification Search
CPC ...................... A61K 31/445; A61K 31/381
See application file for complete search history.

(56) References Cited

U.S. PATENT DOCUMENTS

| | | |
|---|---|---|
| 7,348,325 B2 | 3/2008 | Cai et al. |
| 7,652,009 B2 | 1/2010 | Kim et al. |
| 8,017,611 B2 | 9/2011 | Barlaam et al. |
| 8,288,548 B2 | 10/2012 | Coates et al. |
| 8,580,790 B2 | 11/2013 | Baroni et al. |
| 8,957,211 B2 | 2/2015 | Baroni et al. |
| 9,742,685 B2 | 8/2017 | Cruz-Aguilar et al. |
| 9,742,686 B2 | 8/2017 | Cruz-Aguilar et al. |
| 2006/0106015 A1 | 5/2006 | Sjo et al. |
| 2006/0252777 A1 | 11/2006 | Kim et al. |
| 2009/0197862 A1 | 8/2009 | Steinig et al. |
| 2012/0245149 A1 | 9/2012 | Baroni et al. |
| 2014/0038946 A1 | 2/2014 | Baroni et al. |
| 2015/0089059 A1 | 3/2015 | Cruz-Aguilar et al. |
| 2015/0089060 A1 | 3/2015 | Cruz-Aguilar et al. |
| 2015/0266825 A1 | 9/2015 | Hood et al. |

FOREIGN PATENT DOCUMENTS

| | | |
|---|---|---|
| EP | 2513108 A1 | 10/2012 |
| JP | 2004-210774 A | 7/2004 |
| JP | 2008-521900 A | 6/2008 |
| KR | 10-2001-0085309 A | 9/2001 |
| KR | 10-2009-0107807 A | 10/2009 |
| KR | 10-2010-0089090 A | 8/2010 |
| KR | 10-2012-0100845 A | 9/2012 |
| KR | 10-2013-0093140 A | 8/2013 |
| WO | 2004/016600 A1 | 2/2004 |
| WO | 2009/126003 A2 | 10/2009 |
| WO | 2011/080444 A1 | 7/2011 |
| WO | 2015/043380 A1 | 4/2015 |

OTHER PUBLICATIONS

Extended European Search Report from European Application No. 17881667.4, dated Oct. 25, 2019.
International Search Report and Written Opinion from International Application No. PCT/KR2017/014893, dated Mar. 21, 2018.
Yakugaku Zasshi, "Ischemic Brain Injury and Hepatocyte Growth Factor", The Pharmaceutical Society of Japan, 2007, 127(11), p. 1813-1823.
Office Action from Japanese Application No. 2019-532126, dated April.

*Primary Examiner* — Raymond J Henley, III
(74) *Attorney, Agent, or Firm* — Merchant & Gould P.C.

(57) ABSTRACT

The present invention relates to a pharmaceutical composition the prevention or treatment of DYRK-related diseases containing a pyridine-based compound as an active ingredient, a pyridine-based compound of the present invention which is used as an active ingredient of the pharmaceutical composition inhibits the activity of DYRK1A with very high efficacy and selectivity, thereby can be used effectively in the prevention or treatment of DYRK-related diseases, such as Down syndrome, degenerative brain diseases, cancer, and metabolic diseases.

8 Claims, 6 Drawing Sheets

PHARMACEUTICAL COMPOSITION FOR PREVENTING OR TREATING DYRK-RELATED DISEASES, CONTAINING PYRIDINE-BASED COMPOUND AS ACTIVE INGREDIENT

This application is a National Stage Application of International Application No. PCT/KR2017/014893, filed Dec. 15, 2017, which claims benefit of Serial No. 10-2017-0172214, filed Dec. 14, 2017 in the Republic of Korea, and claims benefit of Serial No. 10-2016-0171495, filed Dec. 15, 2016 in the Republic of Korea, and which applications are incorporated herein by reference. To the extent appropriate, a claim of priority is made to each of the above disclosed applications.

TECHNICAL FIELD

The present invention relates to a pharmaceutical composition for the prevention or treatment of DYRK-related diseases, the composition containing a pyridine-based compound as an active ingredient.

BACKGROUND ART

Dual-specificity tyrosine phosphorylation-regulated kinase (DYRK) is a serine/threonine kinase, is very highly conserved in evolution, and plays a variety of roles in the central nervous system development and function. Humans have five types of isoforms, such as DYRK1A, DYRK1B, DYRK2, DYRK3, and DYRK4, among these, DYRK1A has been widely studied and has received the most interest related to Down syndrome and degenerative brain diseases. A DYRK1A gene is localized in the Down Syndrome Critical Region (DSCR) of human chromosome 21. As the DYRK1A gene turns out to be a decisive factor in cognitive impairment which typically appears in patients with Down syndrome, the DYRK1A gene has received more interest. Patients with Down syndrome suffer from cognitive impairment and memory impairment, which mainly appear in Alzheimer's disease from around 35-40 years of age. Interestingly, the expression and activity increase of DYRK1A is shown in patients with degenerative brain diseases, such as Alzheimer's disease, Parkinson's disease, Huntington's disease, and Pick's disease, as well as Down syndrome.

Alzheimer's disease is largely accompanied by the two types of neuropathology: an amyloid plaque which is a cell accumulation of the insoluble precipitate of amyloid β peptide; and the formation of the intracellular neurofibrillary tangles consisting of an aggregate of the hyperphosphorylated tau. It is known that DYRK1A directly phosphorylates key proteins in the formation of these neuropathologies, such as Tau, amyloid β precursor protein (APP), and Presenilin 1 (PS1), and thus DYRK1A is associated with Alzheimer's disease. In addition, DYRK1A plays an important role in other degenerative brain diseases, and it is confirmed that DYRK1A affects the formation of Lewy body which is the core neuropathology of Parkinson's disease, through the phosphorylation of α-synuclein, and affects the onset of Huntington's disease through the phosphorylation of HIP-1. These facts show that DYRK1A contributes to the formation of various neuropathologies through the phosphorylation of Tau, APP, PS1, α-synuclein, HIP-1, etc. and results in the cognitive and memory impairment in a variety of degenerative brain diseases, as well as Down syndrome.

In fact, a transgenic mouse model which overexpresses DYRK1A of human or mouse shows the phenotype of Down syndrome, including deficiency and developmental delays of spatial learning and motor neuron that depend on the hippocampus, which implies an important function of DYRK1A in the mental retardation associated with Down syndrome.

The existing FDA-approved drugs as a therapeutic agent for Alzheimer's disease mainly act in a manner to improve the abnormality of the neurotransmitter and have a limited effect to alleviate some of the symptoms of the disease. Future drug development strategy requires a more fundamental treatment approach in such a manner to inhibit the amyloid plaque, the neurofibrillary tangles, etc. directly associated with the onset of Alzheimer's disease. However, it is a widely-accepted theory that it is also difficult to expect that this existing fundamental approach has an adequate therapeutic effect with only improvement for a single neuropathology, thereby there is a need for the new strategy of the multi-target method which can control the amyloid plaque and the neurofibrillary tangles at the same time.

In view of this, the present inventors have tried to develop a drug to target DYRK1A during the study of the strategy to control the amyloid plaque and the neurofibrillary tangles at the same time, have confirmed that the pyridine-based compound according to the present invention is structurally different from the existing known DYRK1A inhibitory substance, the inhibitory effect is more excellent, and the selectivity for DYRK1A is excellent, and have completed the present invention.

In addition, according to a recent study, DYRK1A also receives an interest as a target in developing therapeutic agents for type 1 diabetes other than Down syndrome and degenerative brain diseases. It was confirmed by several research groups that DYRK1A is involved in the proliferation control of the beta cells, which are the insulin-producing cells of the pancreas, through NFAT signaling, and when DYRK1A is inhibited, the proliferation of these cells is activated. After all, an effective inhibitory drug of DYRK1A promotes insulin production and secretion by activating the proliferation of pancreatic beta cells, and thus a therapeutic effect in patients with type 1 diabetes can be expected.

In addition, DYRK1A is highly expressed in a few cancer species, the typical examples of which are brain tumors and hematologic cancers. DYRK1A is reported to be involved in the generation and progression of cancer through the phosphorylation of intracellular various factors (p27, cyclin Dl, DREAM, C-myc, Sprouty, etc.). In particular, Sprouty is an important factor in regulating the recycling of EGFR which is important for the maintenance of the stemness of cancer stem cells, and the anticancer effect can be expected in a manner to inhibit the stemness of the cancer stem cells by inhibiting DYRK1A.

The compound derived from the present invention shows a relatively high inhibitory effect on DYRK1A, but the inhibitory effect is also confirmed on DYRK1B, DYRK3, and DYRK4, and thus the anticancer effect can be expected through the control of the cell cycle in which these isoforms are known to be mainly involved.

DISCLOSURE OF THE INVENTION

Technical Problem

The purpose of the present invention is to provide a pharmaceutical composition that can be used to prevent or treat DYRK-related diseases, such as Down syndrome, degenerative brain diseases, cancer diseases, and metabolic diseases.

Technical Solution

In order to achieve the above purpose, the present invention provides a pharmaceutical composition for the prevention or treatment of DYRK-related diseases, including a compound or a pharmaceutically acceptable salt thereof represented by formula 1 below as an active ingredient.

[Formula 1]

(In the formula above, $R^1$, $R^2$, $R^3$, $R^4$ and $R^5$ are as defined in the present invention.)

Advantageous Effects

A compound represented by formula 1 according to the present invention has not only a strong inhibitory activity on DYRK1A, but also a high selectivity for DYRK protein, and thus may be used effectively in the prevention or treatment of DYRK-related diseases, such as Down syndrome, degenerative brain diseases, cancer diseases, and metabolic diseases.

MODE FOR CARRYING OUT THE INVENTION

Hereinafter, the present invention will be described in detail.

The present invention provides a compound represented by formula 1 below.

[Formula 1]

In formula 1 above, $R^1$ may be a hydrogen or $-NR^6R^7$. Here, $R^6$ and $R^7$ are each independently a hydrogen, a $C_1$-$C_5$ straight or branched chain alkyl or benzyl, specifically, $R^6$ and $R^7$ may be each independently a hydrogen, or a $C_1$-$C_3$ straight or branched chain alkyl.

In formula 1 above, $R^2$, $R^3$ and $R^4$ may be each independently a hydrogen, a halogen, a $C_1$-$C_5$ straight or branched chain alkyl, $-NR^8R^9$, $OR^8$, $-CN$, $-NHC(O)$ $R^8$, $-SO_2R^8$, $-OS(O)_2R^8$, pyrrolidine, piperidine, or morpholin, specifically, $R^2$, $R^3$ and $R^4$ may be each independently a hydrogen, $-F$, $-Cl$, $-Br$, $-I$, a $C_1$-$C_3$ straight or branched chain alkyl, $-NR^8R^9$, $OR^8$, $-CN$, $-NHC(O)R^8$, $-SO_2R^8$, $-OS(O)_2R^8$, pyrrolidine, piperidin or morpholin, and more specifically, $R^2$, $R^3$ and $R^4$ may be each independently a hydrogen, $-F$, $-Cl$, $-Br$, $-I$, a $C_1$-$C_3$ straight or branched chain alkyl. Here, $R^8$ and $R^9$ may be each independently a hydrogen, a $C_1$-$C_5$ straight or branched chain alkyl, a $C_1$-$C_5$ straight or branched chain alkynyl, a $C_6$-$C_{12}$ straight or branched chain alkenyl, a $C_6$-$C_{12}$ aryl, a $C_6$-$C_{12}$ aryl substituted with a halogen, or a $C_6$-$C_{12}$ aryl substituted with a trihalogen methyl, specifically, $R^8$ and $R^9$ may be each independently a hydrogen, a $C_1$-$C_5$ straight or branched chain alkyl.

In formula 1 above, $R^5$ may be a hydrogen, a $C_1$-$C_5$ straight or branched chain alkyl, unsubstituted 4-piperidine, acetyl-substituted 4-piperidin, specifically, $R^5$ may be a hydrogen, a $C_1$-$C_3$ straight or branched chain alkyl, unsubstituted 4-piperidine or acetyl-substituted 4-piperidin.

In formula 1, A may be a carbon or a nitrogen, specifically, the A may be a nitrogen.

The compound may be a compound represented by formula 1, a compound represented by formula 2, a compound represented by formula 3, or a compound represented by formula 4.

[Formual 2]

[Formual 3]

[Formual 4]

The compound represented by formula 1 of the present invention has the effect of inhibiting the activity of DYRK. In specific embodiments of the present invention, it was confirmed that the compound represented by formula 1 strongly inhibits DYRK1A with selectivity, and the phosphorylation of Tau protein which is a representative DYRK1A substrate-protein and the core factor of the formation of neurofibrillary tangle is inhibited. It is confirmed through molecular modeling that the inhibitory action is performed in a competitive manner with ATP. From the results as described above, it may be seen that the compound represented by formula 1 of the present invention may be used as an active ingredient of a pharmaceutical composition the prevention or treatment of DYRK-related diseases.

Accordingly, the present invention provides a pharmaceutical composition for the prevention or treatment of DYRK-related diseases, including a compound or a pharmaceutically acceptable salt thereof represented by formula 1 as an active ingredient.

The "prevention" refers to reducing the risk of the onset of a disease or a disorder, that is, not allowing one or more clinical symptoms of the disease to progress in a subject who is exposed to the disease, or susceptible to the disease, but does not yet suffer from the disease and represent the symptoms of the disease. The "treatment" refers to alleviating the disease or the disorder, that is, preventing or reducing the progression of the disease or one or more clinical symptoms thereof.

The DYRK-related diseases may mean a disease caused by over-expression and hyperactivation of DYRK, for example, Down syndrome, degenerative brain diseases, cancer diseases, metabolic diseases, etc.

The degenerative brain disease may be at least one disease selected from the group consisting of Pick's disease, vascular dementia, Alzheimer's disease, Parkinson's disease, Lewy body dementia, frontotemporal dementia, Creutzfeld-Jakob, Huntington's chorea, multiple sclerosis, Guillain-Barre syndrome.

The cancer disease may be selected from the group consisting of lung cancer, bone cancer, pancreatic cancer, skin cancer, head and neck cancer, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphoma, cancer of the bladder, cancer of the kidney or ureter, renal cell carcinoma, carcinoma of the renal pelvis, neoplasm of the central nervous system (CNS), primary CNS lymphoma, spinal axis tumor, brain stem glioma, pituitary adenoma.

Furthermore, the metabolic disease may be selected from the group consisting of obesity, diabetes, hypertension, hyperlipidemia, hypercholesterolemia, arteriosclerosis, fatty liver, heart disease, myocardial infarction, angina.

In specific embodiments of the present invention, it was confirmed that a compound represented by formula 1 of the present invention effectively inhibits DYRK1A, thereby regulating neurofibrillary tangles, an amyloid plaque, the formation of Lewy body by controlling the phosphorylation of Tau, APP, PS1, α-synuclein, HIP1, etc., and eventually, the composition may be used to prevent or treat DYRK-related diseases, such as various degenerative brain diseases, including Alzheimer's disease.

The "pharmaceutically acceptable salt" refers to a salt of the compounds of the present invention which is pharmaceutically acceptable and has the desired pharmacological activity of the parent compound. Such a salt may be prepared by typical methods in the art, for example, a salt of an inorganic acid, such as hydrochloric acid, hydrobromic acid, sulfuric acid, sodium hydrogen sulfate, phosphoric acid, nitric acid, and carbonic acid, a salt of an organic acid, such as formic acid, acetic acid, propionic acid, oxalic acid, succinic acid, benzoic acid, citric acid, maleic acid, malonic acid, tartaric acid, gluconic acid, lactic acid, gentisic acid, fumaric acid, lactobionic acid, salicylic acid, or acetylsalicylic acid (aspirin), a salt of an amino acid, such as glycine, alanine, valine, isoleucine, serine, cysteine, cystine, aspartic acid, glutamine, lysine, arginine, tyrosine, proline, a salt of a sulfonic acid, such as methanesulfonic acid, ethanesulfonic acid, benzenesulfonic acid, toluenesulfonic acid, a metal salt by the reaction with the alkali metal, such as sodium, potassium, or a salt of the ammonium ion.

The pharmaceutical composition according to the present invention may be formulated by the addition of nontoxic and pharmaceutically acceptable carriers, adjuvants, excipients, etc. in a typical manner, for example, formulations, such as tablets, capsules, troches, liquid medicines, and suspension agents for oral administration or for parenteral administration.

In addition, the excipient that may be used in the pharmaceutical composition according to the present invention includes sweeteners, binders, solubilizers, dissolution aids, wetting agents, emulsifiers, isotonic agents, sorbents, disintegrates, antioxidants, preservatives, lubricants, fillers, fragrances, etc., for example, lactose, dextrose, sucrose, mannitol, sorbitol, cellulose, glycine, silica, talc, stearic acid, sterin, magnesium stearate, magnesium aluminum silicate, starch, gelatin, tragacanth, alginate, sodium alginate, methyl cellulose, sodium carboxymethyl cellulose, agar, water, ethanol, polyethylene glycol, polyvinylpyrrolidone, ammonium chloride, calcium chloride, orange essence, strawberry essence, vanilla flavor, and the like.

The compound of the present invention may be included in a concentration level of a range of 0.1% to 95% by weight based on the total weight of the pharmaceutical composition, i.e., an amount sufficient to obtain the desired effect.

The pharmaceutical composition of the present invention may be used in the form of oral formulations, such as powder, granules, tablets, capsules, suspensions, emulsions, syrups, and aerosols, external preparations, suppositories, or sterile injectable solutions which are formulated in accordance with a typical method.

The pharmaceutical composition including a compound of the present invention may further include suitable carriers, excipients or diluents according to a typical method. Specifically, when formulated the pharmaceutical composition may be prepared using diluents or excipients such as fillers, extenders, binders, wetting agents, disintegrates, and surfactants which are usually used. The solid formulation for oral administration may include tablets, pills, powder, granules, capsules, etc., such a solid formulation may be prepared by mixing at least one excipient, for example, starch, calcium carbonate, sucrose, lactose, gelatin, etc. with the compound. Further, in addition to simple excipients, lubricants, such as magnesium stearate and talc may also be used. The liquid formulation for oral administration is suspensions, internal liquid medicines, emulsions, syrups, etc., and may include various excipients in addition to simple diluents which are commonly used, such as water, liquid paraffin, for example, wetting agents, sweeteners, fragrances, preservatives, etc. Formulations for parenteral administration include sterile aqueous solutions, non-aqueous solvents, suspensions, emulsions, lyophilized formulations, and suppositories. Non-aqueous solvents or suspensions includes propylene glycol, polyethylene glycol, vegetable oil such as olive oil, injectable esters such as ethyl oleate, etc. Bases for suppositories may use witepsol, macrogol, Tween 61, cacao fat, laurin fat, or glycerogelatine.

The pharmaceutical composition of the present invention may be administered by various routes to mammals such as rats, mice, livestock, and human beings. All methods of administration may be anticipated, for example, the composition may be administered by skin, oral, rectal, intravenous, intraperitoneal, intramuscular, subcutaneous, intrauterine dura mater or intracerebroventricular injection, preferably any route of either oral or intravenous, but the present invention is not limited thereto.

One or more types of active ingredients which exhibit the same or similar function may be included in the administration. For administration, the composition may further include one or more types of pharmaceutically acceptable carrier. The pharmaceutically acceptable carriers may include saline, sterile water, Ringer's solution, buffered saline, dextrose solution, maltodextrin solutions, glycerol, ethanol, and a mixture of one or more thereof, and other typical additives, such as antioxidants, buffers, and bacteriostatic agents may be added to the carriers as necessary. In addition, the compound according to the present invention is easy to be formulated in various forms, for example, the compound may be formulated into injectable formulations, such as an aqueous solution, a suspension, and an emulsion, powder, tablets, capsules, pills, granules or injectable solution agents by additionally adding diluents, dispersants, surfactants, binders and lubricants.

The amount of the compound during the administration varies in wide range depending on the weight, age, sex, general health, diet, administration time, administration method, excretion range, and severity of disease of the patient. The daily dose of the compound of the present invention is 0.0001-100 mg/kg, preferably, 0.001-30 mg/kg, and the amount of the compound may be administered once a day or in divided doses several times a day. In addition, the administration period may be one day to two months, but may be administered without limitation until the prevention or treatment effect of the disease appears.

The present invention also provides a health functional food composition for the prevention or improvement of DYRK-related diseases comprising a compound or a pharmaceutically acceptable salt thereof represented by formula 1 as an active ingredient.

The health functional food composition according to the invention may be prepared by adding the compound of formula 1 or a pharmaceutically acceptable salt thereof to a health functional food, such as food, beverages for the purpose of the prevention or improvement of DYRK-related diseases, such as Down syndrome, degenerative brain diseases, cancer diseases, and metabolic diseases.

There is no particular limitation on the type of the food. Examples of foods to which the materials may be added include a drink, meat, sausages, breads, biscuits, rice cakes, chocolates, candies, snacks, confectionery, pizza, ramen, other noodles, gum, dairy products including ice cream, various soups, beverages, alcoholic beverages and vitamin complexes, milk products, milk processed goods and the like, and include all of the health functional foods in a normal sense.

The compounds of formula 1 of the present invention may be added to the foods as it is or may be used with other food or food ingredients, and may be suitably used in a typical manner. The mixing amount of the active ingredients may be suitably determined according to its intended use (for prevention or improvement). In general, the amount of the compound in the health food may be 0.1 to 90 parts by weight of the total food weight. However, in the case of long-term intake for the purpose of health and hygiene, or for the purpose of health control, the amount may be less than the above range. Since there is no problem in terms of safety, the active ingredients may also be used in an amount greater than or equal to the above range.

A health functional beverage composition of the present invention may contain various flavors, natural carbohydrates, or the like as additional ingredients like normal beverages, and other ingredients may be not particularly limited, except for containing the above compound as an essential ingredient in the indicated ratio. Examples of the above-mentioned natural carbohydrates include: monosaccharides, for example, glucose, fructose, etc.; disaccharide, for example, maltose, sucrose, etc.; and polysaccharides, for example, typical sugar, such as dextrin and cyclodextrin, and sugar alcohol, such as xylitol, sorbitol, and erythritol. Natural flavors (Thaumatin, Stevia extract (e.g. rebaudioside A, glycyrrhizin, etc.) and synthetic flavors (saccharin, aspartame, etc.) may be advantageously used as flavors other than the above-mentioned. The proportion of the natural carbohydrates is generally about 1 g to 20 g per 100 g of the composition of the present invention, preferably from about 5 g to 12 g.

The compound of formula 1 of the present invention in addition to the above-mentioned may include a variety of nutrients, vitamins, minerals (electrolytes), flavors such as synthetic flavors and natural flavors, coloring agents and flavor enhancers (cheese, chocolate, etc.), pectic acid and its salts, alginic acid and its salts, organic acids, protective colloid thickeners, pH adjusters, stabilizers, preservatives, glycerin, alcohols, carbonating agents used in the carbonated beverages, etc. In addition, quinoline 4-one derivatives of the present invention may contain a pulp for the production of natural fruit juice, fruit juice beverages and vegetable beverages. These ingredients may be used independently or in combination. The proportion of such additives is generally selected from the range of 0.1 to about 20 parts by weight per 100 parts by weight of the quinoline 4-one derivatives of the present invention, but not so important.

Hereinafter, the present invention will be described in detail by the following experimental examples.

However, the following experimental examples are merely illustrative of the present invention, and the scope of the invention is not limited by the experimental examples.

[Experimental Example 1] Screening of Pyridine-Based Compounds According to the Present Invention In order to find the pyridine-based compound according to the present invention, the virtual screening and the experiment were performed with respect to about 340,000 species of compounds, thereby deriving compounds with DYRK1A-inhibitory effect.

[1-1] Identification of Novel Inhibitors Using Virtual Screening (Primary Screening)

To screen compounds having the expected efficacy to inhibit the DYRK1A target in a large amount of compound libraries, a molecular modeling technique was applied to effectively use the available resources. Simulation using a computer may be divided by two criteria to apply a variety of ways in detail. When the 3D crystal structure of the target protein is known, Structure-Based Drug Design (SBDD) using the three-dimensional structure of the protein may be applied, and when only the structure of the ligand is known, Ligand-Based Drug Design (LBDD) may be applied.

Since the X-ray crystal structure of the target in DYRK1A had been found, the protein structure-based method (Structure-Based Virtual Screening, SBVS) was selected and 340, 000 compounds in Korea Chemical Bank were utilized. Through the three-dimensional structure analysis of the protein of the known 21 X-ray structures, the proteins which are used for considering the space of the binding site, conformation differences, and the variety of inhibitor structure are PDB code 4MQ1 (2.35 Å) and 4YLL (1.4 Å), and pyrido[2,3-d]pyrimidine and indole[3,2-c]quinoline carboxylic acid derivatives are bound to the proteins, respectively. When analyzing the active site, the hydrogen bonding of the hinge region was expected to be an important functional pharmacophore, and thus when the virtual screening was applied, huge 340,000 compound libraries were searched four times by applying two itemized conditions for the selected two protein structures, respectively.

Figure 1:
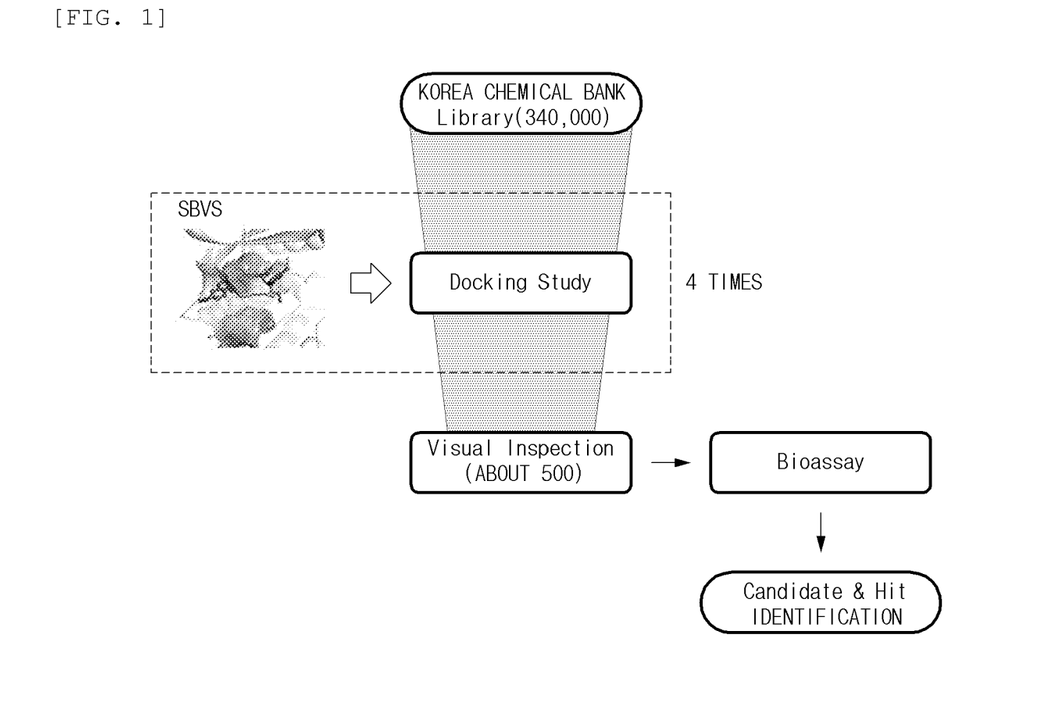
FIG. 1 is a schematic diagram showing a virtual screening process for discovering a DYRK1A inhibitor according to the present invention.
Figure 2:
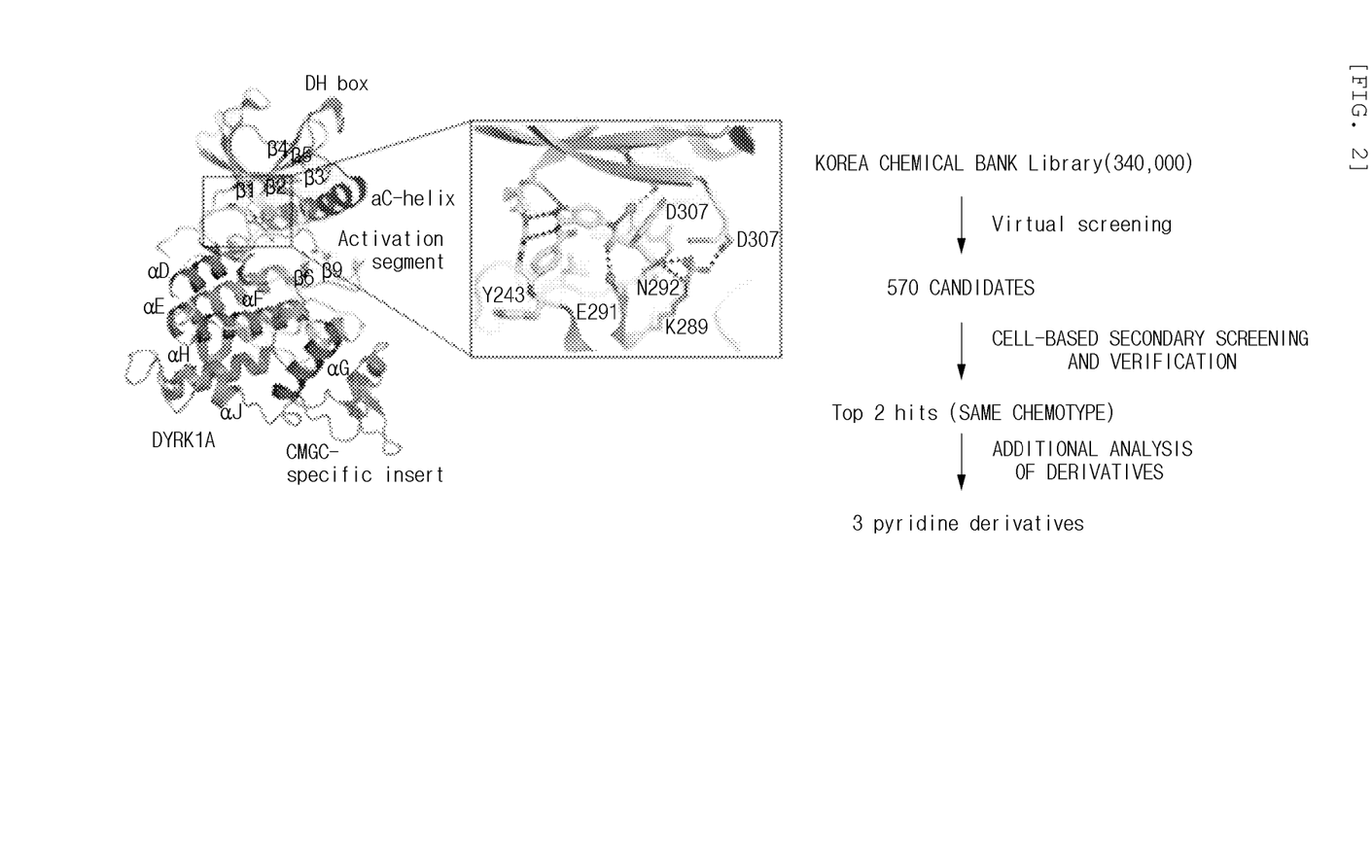
FIG. 2 is a schematic diagram showing a discovery process of three novel pyridine-based DYRK1A inhibitors according to the present invention.

For each of 50,000 compounds that had been screened by applying the proposed-above SBVS method, the compound structure and the prediction coupling mode were analyzed with the maximum consideration of the structural diversity, and thereby selecting 570 compounds with the final eye-selection (FIG. 1). In summary of the subsequent process, two excellent inhibitors having the same chemotype were confirmed through the secondary screening and verification using the cell-based DYRK1A activity evaluation for the 570 candidate drugs, and one inhibitor having the same chemotype was further confirmed through the additional analysis of derivatives, thereby identifying a total of three pyridine-based drugs (FIG. 2).

[1-2] Evaluation of DYRK1A-Inhibitory Effect in Mammalian Cells (Secondary Screening)

Figure 3:
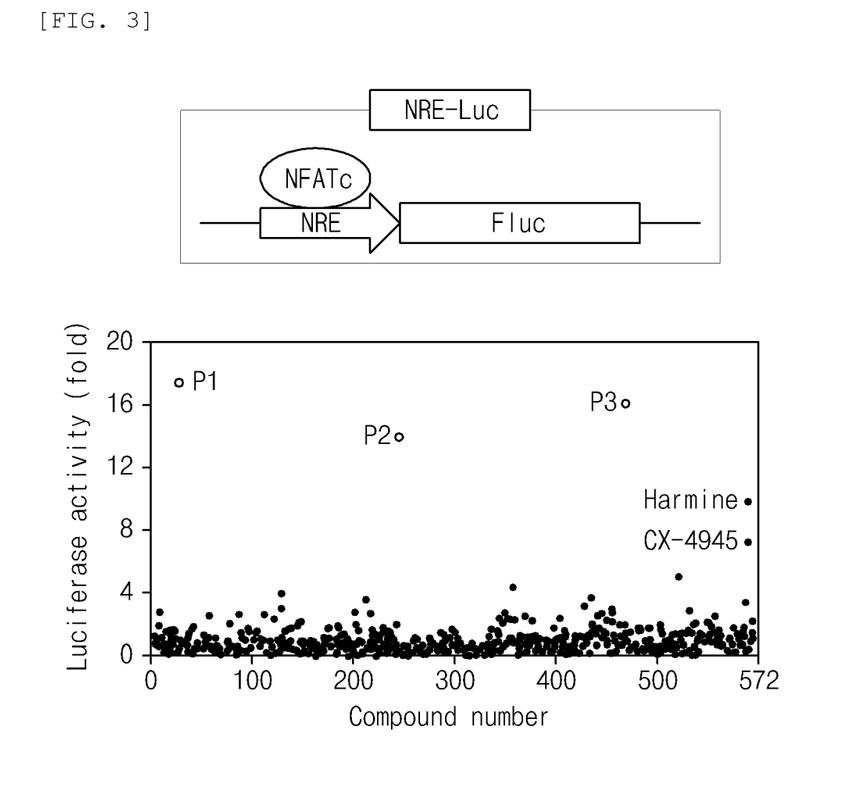
FIG. 3 shows the operation principle of an NFAT signaling reporter which is the cell-based DYRK1A efficacy evaluation system and the results of the secondary efficacy evaluation performed using the operation principle.

With respect to the 570 compounds identified as candidate DYRK1A inhibitors through the virtual screening, a secondary effect evaluation was carried out using NFAT signaling reporter which is the already well-established cell-based DYRK1A effect evaluation system (FIG. 3). NFAT signaling reporter has a very high level of dependence on DYRK1A, and thus is effective in the identifying experiment of the proper candidate DYRK1A inhibitors.

DYRK1A is known to regulate calcineurin/Nuclear Factor of Activated T cells (NFAT) signals and play an important role in the stage of human development process. NFATc1 transcription factor is usually present as a protein that is phosphorylated in the cytoplasm when the $Ca^{2+}$ concentration of the cells is increased, NFATc1 is dephosphorylated by calcineurin phosphatase which is a $Ca^{2+}$-dependent protein, and NFATc1 is moved into the nucleus. NFATc1 which has entered into the nucleus and protein partner NFATn form a transcription complex, and the complex binds to the promoter of the target gene to induce the target gene expression. In contrast, DYRK1A phosphorylates NFATc1 to inhibit the movement of NFATc1 into the nucleus, and results in the inhibition of the expression of the target gene.

The DYRK1A-inhibitory effect of the 570 candidates was confirmed through the transcription activity of NFATc1, and for this, a luciferase reporter containing NFAT response element (NFAT-RE) useful to measure the transcription activity of NFATc1 was used. A NFAT-RE-luciferase reporter was over-expressed in 293T cells, and was then treated with Ionomycin (IM) and phorbol 12-myristate 13-acetate (PMA) to increase the intracellular concentration of $Ca^{2+}$. As a result, the expression of luciferase was increased sharply. It was confirmed that the expression of luciferase was relatively inhibited due to carrying out the overexpression of DYRK1A here. If the candidate drug treatment in this condition inhibits DYRK1A, the luciferase will be increased. In fact, the 570 candidates were treated with 10 μM concentration, as a result, the compounds represented by the above formula 2, 3 and 4 exhibited the highest luciferase increase effect (FIG. 3), and the activity level was clearly higher than that of harmine and CX-4945 which are the existing reported DYRK1A inhibitors.

Finally, the three DYRK1A inhibitors obtained has the pyridine structure in common, in which benzoxazole and pyrazole are structurally coupled, in particular the compound 3 represented by formula 4 is determined to be the minimum unit of the compound having a DYRK1A-inhibitory activity.

Figure 4:
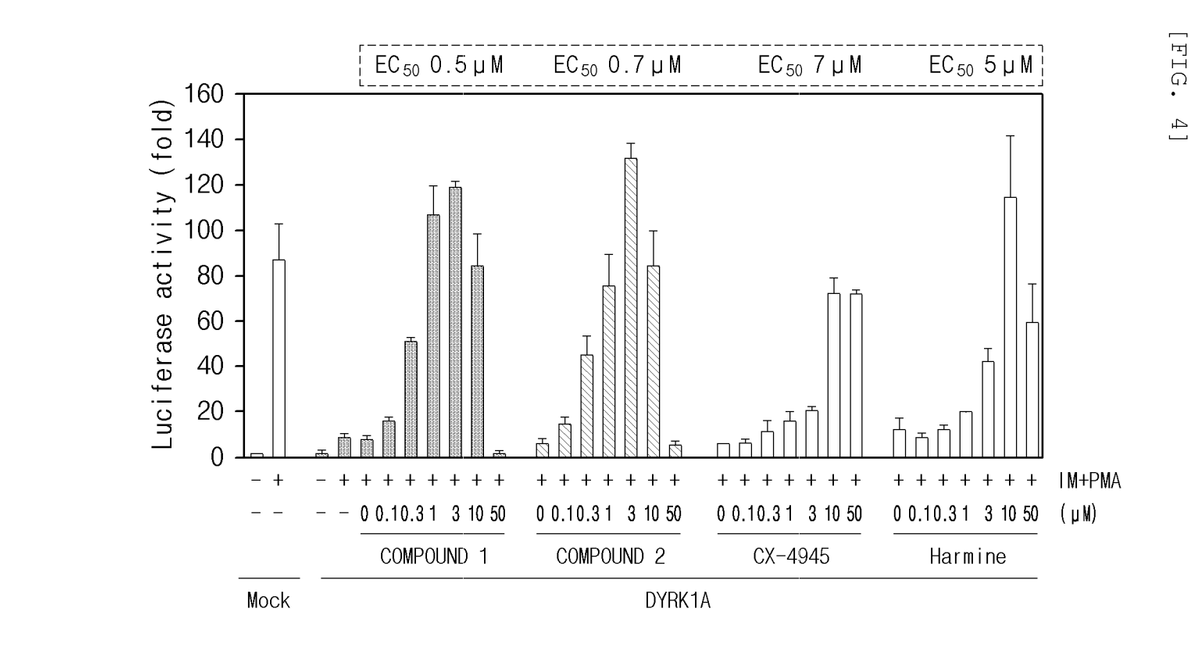
FIG. 4 is an NFAT signaling reporter expression graph confirming the concentration-dependent DYRK1A-inhibitory effect of the compounds represented by formulae 2 and 3, wherein compound 1 represents a compound represented by formula 2, compound 2 represents a compound represented by formula 3.

As a result of the analysis of the effect level of the compounds represented by formulae 2 and 3 in more depth, the luciferase activity when treated with concentration gradient in the same conditions was increased gradually, and when treated with 3 μM, the luciferase activity was higher than the luciferase activity of the condition that DYRK1A was not overexpressed. As mentioned above, the luciferase increase effect of the compounds represented by formulae 2 and 3 shows 10 times lower $EC_{50}$ than that of harmine and CX-4945 which are the existing reported DYRK1A inhibitors, and thus it was confirmed that the compounds represented by formulae 2 and 3 have more excellent effect than these (FIG. 4).

Figure 5:
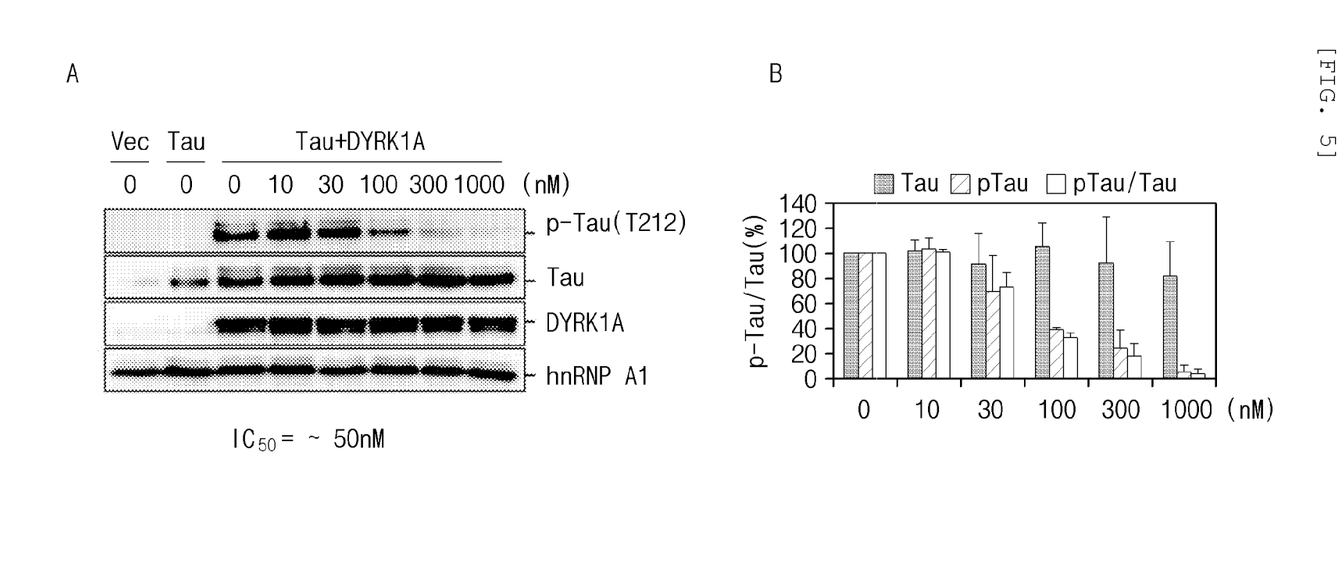
FIG. 5A is a photograph showing the Tau phosphorylation inhibitory effect of the compound represented by formula 2 according to the present invention at a mammalian cell level.
FIG. 5B is a graph showing the Tau phosphorylation inhibitory effect of the compound represented by formula 2 according to the present invention at a mammalian cell level.

[Experimental Example 2] Evaluation of the Inhibitory Effect of Tau Protein Phosphorylation at the Cellular Level In order to more clearly confirm whether the compound represented by formula 2 at the mammalian cell level can inhibit DYRK1A, the phosphorylation of Tau, which is a typical substrate protein of DYRK1A and a main factor of the onset of Alzheimer's disease and Down syndrome was carried out. Tau is a microtubule-related protein, and DYRK1A mainly phosphorylates Thr212 of Tau protein, and this phosphorylation has been clearly observed in the hippocampus tissue of the Down syndrome model mice in which DYRK1A is overexpressed. It was confirmed that the phosphorylation did not appear when only Tau protein was overexpressed in mammalian cell 293T, and when DYRK1A was overexpressed together, the phosphorylation appeared clearly. It was confirmed that as treating the compound represented by formula 2 to this while increasing the concentration of the compound, the phosphorylation of Tau was decreased clearly (FIG. 5). The inhibition of Tau phosphorylation by the compound represented by formula 2 showed a very low $IC_{50}$ of about 50 nM, which is equivalent to the inhibitory effect about 10-60 times stronger than that of harmine ($IC_{50}$=~500 nM), INDY, and proINDY ($IC_{50s}$=~3000 nM) which were tested in the same experimental conditions. These results show that the compound represented by formula 2 at the mammalian cell level has a strong inhibitory effect of DYRK1A.

Figure 6:
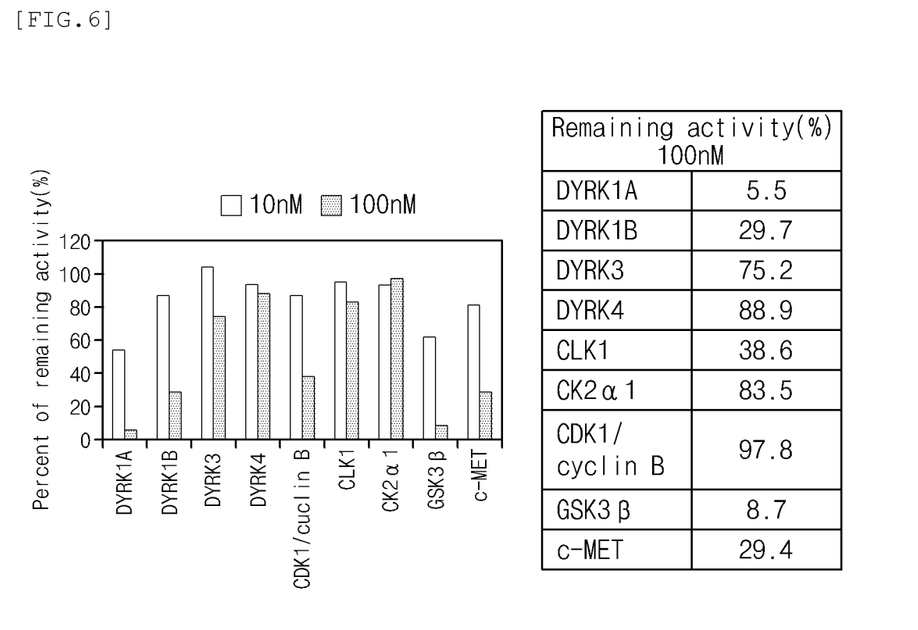
FIG. 6 is a graph showing the in vitro CMGC kinase enzyme activity inhibitory effect of the compound represented by formula 2.

[Experimental Example 3] Confirmation of the Inhibitory Effect of DYRK1A Phosphorylation Activity In Vitro In order to determine whether the compound represented by formula 2 directly inhibits DYRK1A, in vitro kinase assay was carried out using a separated and purified DYRK1A protein, and it was also confirmed whether the compound has the selective effect of DYRK1A, including a typical CMGC kinase, as well as DYRK family kinase such as DYRK1B, DYRK3, and DYRK4. The compound represented by formula 2 exhibited the strongest inhibitory effect on DYRK1A, and showed the inhibitory effect of about 95% at 100 nM concentration; this is a strong inhibitory effect enough to predict approximately 10 nM $IC_{50}$ (FIG. 6). Of note, the compound represented by formula 2 showed a high inhibitory effect on GSK3β next to DYRK1A, GSK3β in addition to DYRK1A is also expected to be able to exhibit a synergistic effect when considering that GSK3β is an important kinase in the formation of amyloid plaque and neurofibrillary tangle which are the main neuropathology of degenerative brain diseases.

[Experimental Example 4] Combined Molecular Modeling Measurement

The compounds represented by formulae 2 and 3 are reported as inhibitors of the C-met kinase in the existing studies, and it has been found to act in an ATP competitive manner. In order to determine in more depth whether the compounds represented by the above formulae 2 and 3 show the inhibitory effect on DYRK1A in an ATP competitive manner, and what binding force acts, docking study between the ATP binding site of DYRK1A and the two compounds was carried out utilizing the molecular modeling techniques using a computer.

Figure 7:
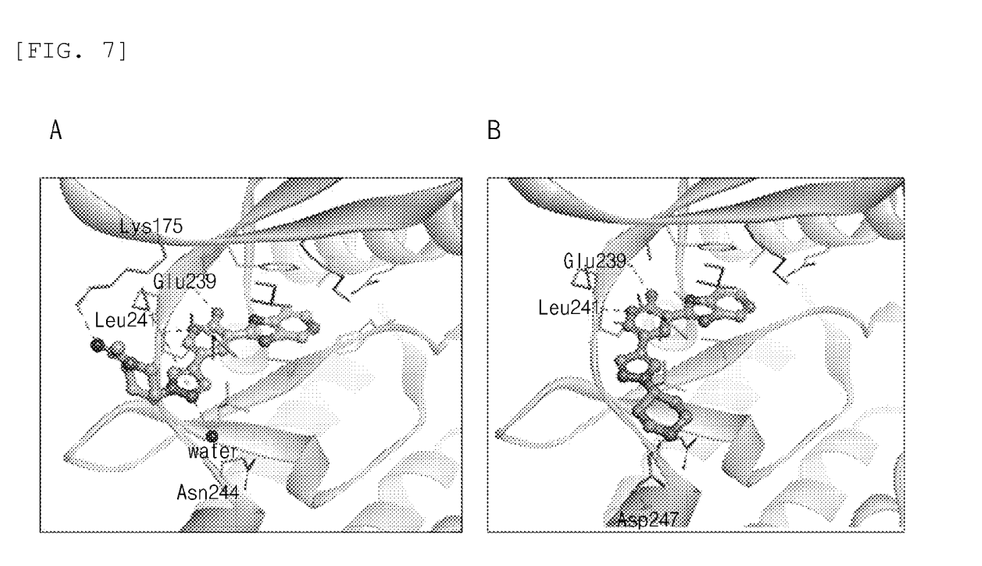
FIG. 7 is a diagram showing a prediction model of the combined structure of DYRK1A and the compounds represented by formulae 2 and 3, wherein compound 1 represents a compound represented by formula 2, and compound 2 represents a compound represented by formula 3.

According to FIG. 7 showing the results, the compounds represented by formulae 2 and 3, each of the compounds structurally fits well to the ATP binding site of DYRK1A, in particular, it is predicted that a hydrogen bond formed between a nitrogen of the pyridine ring and Leu241 and Glu239 of DYRK1A hinge region plays an important role.

Although the preferred embodiments of the present invention have been disclosed for illustrative purposes, the scope of the present invention is not limited to the particular embodiments as described above, it will be understood by those skilled in the art that various changes in form and details may be made therein without departing from the spirit and scope of the invention as defined by the appended claims.

The invention claimed is:

1. A method for treating or improving DYRK-related diseases in a subject in need thereof comprising:
a compound or a pharmaceutically acceptable salt thereof represented by formula 1 below as an active ingredient:

[Formual 1]

(in formula 1 above,
$R^1$ is a hydrogen or —$NR^6R^7$, wherein $R^6$ and $R^7$ are each independently a hydrogen, a $C_1$-$C_5$ straight or branched chain alkyl or benzyl;
$R^2$, $R^3$ and $R^4$ are each independently a hydrogen, a halogen, a $C_1$-$C_5$ straight or branched chain alkyl, —$NR^8R^9$, $OR^8$, —CN, —NHC(O)$R^8$, —$SO_2R^8$, —OS(O)$_2R^8$, pyrrolidine, piperidine, or morpholin, wherein $R^8$ and $R^9$ are each independently a hydrogen, a $C_1$-$C_5$ straight or branched chain alkyl, a $C_1$-$C_5$ straight or branched chain alkynyl, a $C_6$-$C_{12}$ straight or branched chain alkenyl, a $C_6$-$C_{12}$ aryl, a $C_6$-$C_{12}$ aryl substituted with a halogen, or a $C_6$-$C_{12}$ aryl substituted with a trihalogen methyl; and
$R^5$ is a hydrogen, a $C_1$-$C_5$ straight or branched chain alkyl, unsubstituted 4-piperidine, acetyl-substituted 4-piperidin;
wherein the DYRK-related disease is at least one disease selected from the group consisting of Down syndrome, degenerative brain diseases and metabolic diseases.

2. The method of claim 1, wherein $R^1$ is a hydrogen or —$NR^6R^7$, wherein $R^6$ and $R^7$ are each independently a hydrogen, a $C_1$-$C_3$ straight or branched chain alkyl;
$R^2$, $R^3$ and $R^4$ are each independently a hydrogen, —F, —Cl, —Br, —I, a $C_1$-$C_3$ straight or branched chain alkyl, —$NR^8R^9$, $OR^8$, —CN, —NHC(O)$R^8$, —$SO_2R^8$, —OS(O)$_2R^8$, pyrrolidine, piperidin or morpholin, wherein $R^8$ and $R^9$ are each independently a hydrogen, a $C_1$-$C_5$ straight or branched chain alkyl;
$R^5$ is a hydrogen, a $C_1$-$C_3$ straight or branched chain alkyl, unsubstituted 4-piperidine or acetyl-substituted 4-piperidin.

3. The method of claim 1, wherein $R^1$ is a hydrogen or —$NR^6R^7$, wherein $R^6$ and $R^7$ are each independently a hydrogen, a $C_1$-$C_3$ straight or branched chain alkyl;
$R^2$, $R^3$ and $R^4$ are each independently a hydrogen, —F, —Cl, —Br, —I, a $C_1$-$C_3$ straight or branched chain alkyl;
$R^5$ is a hydrogen, a $C_1$-$C_3$ straight or branched chain alkyl, unsubstituted 4-piperidine or acetyl-substituted 4-piperidin.

4. The method of claim 1, the degenerative brain disease is Pick's disease, vascular dementia, Alzheimer's disease, Parkinson's disease, Lewy body dementia, frontotemporal dementia, Creutzfeld-Jakob, Huntington's chorea, multiple sclerosis, Guillain-Barre syndrome and Down syndrome.

5. The pharmaceutical composition of claim 1, the metabolic disease is selected from the group consisting of obesity, diabetes, hypertension, hyperlipidemia, hypercholesterolemia, arteriosclerosis, fatty liver, heart disease, myocardial infarction, angina.

6. A method for inhibiting an activity of a DYRK1A in a subject in need thereof comprising:
administering a composition to the subject, wherein the composition comprising a compound or a pharmaceutically acceptable salt thereof represented by the following formula (1) as an active ingredient:

[Formual 1]

(in formula 1,
$R^1$ is a hydrogen or —$NR^6R^7$, wherein $R^6$ and $R^7$ are each independently a hydrogen, a $C_1$-$C_5$ straight or branched chain alkyl or benzyl;

$R^2$, $R^3$ and $R^4$ are each independently a hydrogen, a halogen, a $C_1$-$C_5$ straight or branched chain alkyl, —$NR^8R^9$, $OR^8$, —CN, —NHC(O)$R^8$, —SO$_2R^8$, —OS(O)$_2R^8$, pyrrolidine, piperidine, or morpholin, wherein $R^8$ and $R^9$ are each independently a hydrogen, a $C_1$-$C_5$ straight or branched chain alkyl, a $C_1$-$C_5$ straight or branched chain alkynyl, a $C_6$-$C_{12}$ straight or branched chain alkenyl, a $C_6$-$C_{12}$ aryl, a $C_6$-$C_{12}$ aryl substituted with a halogen, or a $C_6$-$C_{12}$ aryl substituted with a trihalogen methyl;

$R^5$ is a hydrogen, a $C_1$-$C_5$ straight or branched chain alkyl, unsubstituted 4-piperidine, acetyl-substituted 4-piperidin.

7. The method of claim 6 wherein $R^1$ is a hydrogen or —$NR^6R^7$, wherein $R^6$ and $R^7$ are each independently a hydrogen, a $C_1$-$C_3$ straight or branched chain alkyl;

$R^2$, $R^3$ and $R^4$ are each independently a hydrogen, —F, —Cl, —Br, —I, a $C_1$-$C_3$ straight or branched chain alkyl, —$NR^8R^9$, $OR^8$, —CN, —NHC(O)$R^8$, —SO$_2R^8$, —OS(O)$_2R^8$, pyrrolidine, piperidin or morpholin, wherein $R^8$ and $R^9$ are each independently a hydrogen, a $C_1$-$C_5$ straight or branched chain alkyl;

$R^5$ is a hydrogen, a $C_1$-$C_3$ straight or branched chain alkyl, unsubstituted 4-piperidine or acetyl-substituted 4-piperidin.

8. The method of claim 6 wherein $R^1$ is a hydrogen or —$NR^6R^7$, wherein $R^6$ and $R^7$ are each independently a hydrogen, a $C_1$-$C_3$ straight or branched chain alkyl;

$R^2$, $R^3$ and $R^4$ are each independently a hydrogen, —F, —Cl, —Br, —I, a $C_1$-$C_3$ straight or branched chain alkyl;

$R^5$ is a hydrogen, a $C_1$-$C_3$ straight or branched chain alkyl, unsubstituted 4-piperidine or acetyl-substituted 4-piperidin.

* * * * *

UNITED STATES PATENT AND TRADEMARK OFFICE
CERTIFICATE OF CORRECTION

PATENT NO. : 10,765,669 B2  
APPLICATION NO. : 16/470014  
DATED : September 8, 2020  
INVENTOR(S) : Sungchan Cho et al.

Page 1 of 1

It is certified that error appears in the above-identified patent and that said Letters Patent is hereby corrected as shown below:

In the Claims

Column 12, Line 22: "a compound or a" should read --administering a composition to the subject, wherein the composition comprising a compound or a--

Signed and Sealed this  
Fifth Day of January, 2021

Andrei Iancu  
*Director of the United States Patent and Trademark Office*